United States Patent [19]

Kiener et al.

[11] Patent Number: 5,306,625
[45] Date of Patent: Apr. 26, 1994

[54] PROCESS FOR TERMINAL HYDROXYLATION OF ETHYL GROUPS ON AROMATIC 5- OR 6-RING HETEROCYCLES

[75] Inventors: Andreas Kiener, Visp; Thomas Zimmermann, Naters, both of Switzerland

[73] Assignee: Lonza Ltd., Gampel/Valais, Switzerland

[21] Appl. No.: 101,098

[22] Filed: Aug. 3, 1993

Related U.S. Application Data

[63] Continuation of Ser. No. 846,900, Mar. 6, 1992, abandoned.

[30] Foreign Application Priority Data

Mar. 7, 1991 [CH] Switzerland .............. 696/91

[51] Int. Cl.$^5$ .......... C12P 1/00; C12P 13/06; C12N 15/00; C12N 1/20
[52] U.S. Cl. .................. 435/41; 435/117; 435/122; 435/123; 435/130; 435/156; 435/170; 435/252.3; 435/320.1; 536/18.7; 536/23.1
[58] Field of Search ........... 435/41, 117, 122, 123, 435/130, 156, 170, 252.34, 320.1; 536/18.7, 23.1, 23.2

[56] References Cited

U.S. PATENT DOCUMENTS 5,032,512 7/1991 Witholt et al. .......... 435/123

FOREIGN PATENT DOCUMENTS 277674 8/1988 European Pat. Off. .

OTHER PUBLICATIONS

Withholt et al., Tibtech, vol. 8, (1990), pp. 46 to 52.
Ausubel et al., "Current Protocols In Molecular Biology", Eds., J. Wiley, New York, (1989), Section 1.7
Kok, M., et al., J. Biol. Chem., 264, (1989), pp. 5442 to 5451.
Grund et al., J. Bacteriol., (1975), 123, pp. 546 to 556.
Kulla et al., Arch. Microbiol., 135, (1983), pp. 1 to 7.
Gene, 26, (1983), pp. 273 to 282.
Gene, 18, (1982), pp. 289 to 296.
J. Biol. Chem., 262, (1987), pp. 17712 to 17718.
Maniatis et al., Molecular Cloning, (1989), Cold Sring Harbour Laboratory Press, Sections 1.75 and 5.40 to 5.43.

*Primary Examiner*—Robert A. Wax
*Assistant Examiner*—Miguel H. Escallon
*Attorney, Agent, or Firm*—Fisher, Christen & Sabol

[57] ABSTRACT

A microbiological process for terminal hydroxylation of ethyl groups on aromatic 5- or 6-member ring heterocycles. The hydroxylation is performed with microorganisms which:
(a) contain the genes of a Pseudomonas OCT plasmid which form an active alkane monooxygenase, and
(b) form no active chromosomal or plasmid-coded alcohol dehydrogenase.

21 Claims, 3 Drawing Sheets

PROCESS FOR TERMINAL HYDROXYLATION OF ETHYL GROUPS ON AROMATIC 5- OR 6-RING HETEROCYCLES

This application is a continuation of prior U.S. application Ser. No. 07/846,900, filing date Mar. 6, 1992, now abandoned.

BACKGROUND OF THE INVENTION

1. Field Of The Invention

The invention relates to a new microbiological process for terminal hydroxylation of ethyl groups on aromatic 5- or 6-member ring heterocycles as well as a new hybrid plasmid for the process.

2. Background Art

It is known that the biochemical oxidation of alkanes in microorganisms of genus *Pseudomonas oleovorans* takes place in three steps. By action of the alkane hydroxylase complex, (alkBA genes, which are designated below as alkBFGH genes) first the corresponding alcohol results, which then in two further steps, that is, catalyzed by an alcohol dehydrogenase (alkC genes) and an aldehyde dehydrogenase (chromosomal or plasmid-coded), is converted to the acid. In this strain, the genes, which are responsible for the enzymes of the oxidation, are on the OCT plasmid [Witholt et al., TIBTECH, Vol. 8, (1990), pages 46 to 52].

Further, a microbiological process is known from European Published Patent Application No. 277674 for the terminal hydroxylation of apolar aliphatic compounds with 6 to 12 C-atoms, such as, the production of 1-octanol by microorganisms of the genus *Pseudomonas oleovorans* or *Pseudomonas putida*, which are resistant against apolar phases. As can be seen from the embodiment, it is necessary that the hydroxylation of these compounds be performed in a costly two-phase system.

2-Hydroxyethyl derivatives of 5- or 6-member ring heterocycles are also difficult to access by chemical processes.

BROAD DESCRIPTION OF THE INVENTION

The main object of the invention consequently is to provide a simple microbiological process for terminal hydroxylation of ethyl groups on aromatic 5- or 6-member ring heterocycles, and a hybrid plasmid. Other objects and advantages of the invention are set out herein or are obvious herefrom to one skilled in the art.

The objects and advantages of the invention are achieved by the process and the hybrid plasmid of the invention.

The invention involves a microbiological process for the terminal hydroxylation of ethyl groups on aromatic heterocycles. The reaction is performed with microorganisms, which:

(a) contain the genes of a Pseudomonas OCT plasmid which form an active alkane monooxygenase, and (b) form no active chromosomal or plasmid-coded alcohol dehydrogenase, and, thus, are capable of hydroxylating ethyl groups from aromatic 5- or 6-member ring heterocycles to the corresponding hydroxyethyl derivative. The heterocycle is used as substrate for the reaction. The hydroxyethyl derivative is not further metabolized.

Preferably the reaction is performed with microorganisms which contain the alkBA genes of a Pseudomonas OCT plasmid. Preferably the reaction is performed with microorganisms, which belong to the genus Pseudomonas, Acinetobacter, Rhizobium, Agrobacterium or Escherichia. Preferably the reaction is performed either with *E. coli* DH1 (CBS 102-87) or with *E. coli* DH1 (DSM 6726), both transformed with hybrid plasmid pGEc41, or an active mutant of these strains. Preferably the reaction is performed either with *Pseudomonas putida* PpS81 (DSM6776) or with *Pseudomonas putida* GPO12 (DSM 6775), both transformed with hybrid plasmid pGMK921, or with an active mutant of these strains. Preferably the substrate is an ethylated, aromatic 5- or 6-member ring heterocycle, which contains one or more heteroatoms which is oxygen, nitrogen and/or sulfur. Preferably the substrate is an ethylated pyrazine or ethylated pyridine. Preferably the enzymes of the microorganisms are induced either with compounds which are used by the microorganism as a carbon and energy source, or with compounds which are not used by the microorganism as a carbon and energy source. Preferably the reaction takes place with single or continuous substrate addition, so that the substrate addition does not exceed 20 percent (w/v). Preferably the reaction is performed at a pH of 4 to 11. Preferably the reaction is performed at a temperature of 15° to 50° C.

2-Hydroxyethyl derivatives are important intermediate products for the production of pharmaceutical active ingredients, such as, 2-(4-pyridyl)ethanol for the production of penicillic acid derivatives.

The invention also involves hybrid plasmid pGMK921, as deposited in *Pseudomonas putida* PpS81 (DSM 6776) or in *Pseudomonas putida* GPO12 (DSM 6775).

DETAILED DESCRIPTION OF THE INVENTION

Figure 1:
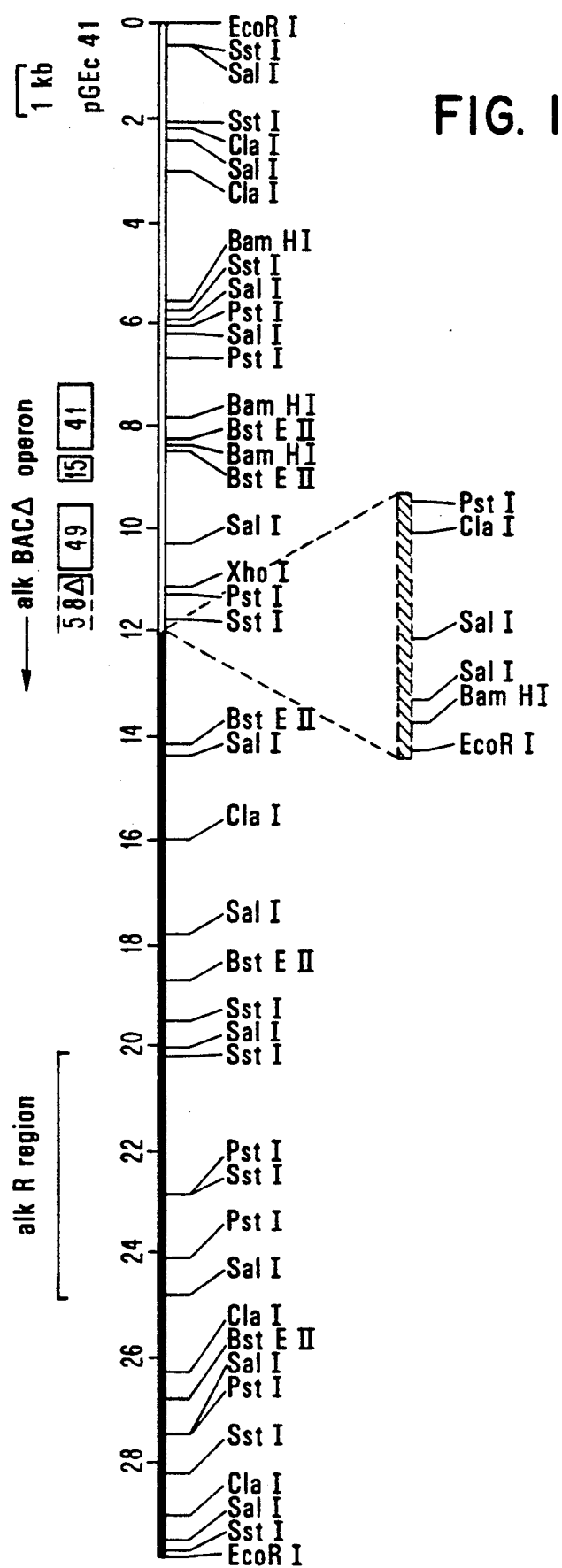
FIG. 1 is restriction map of pGEc41.

According to the invention, the process is performed with microorganisms, which:

(a) contain the genes of a Pseudomonas OCT plasmid which form an active alkane monooxygenase, and (b) form no active chromosomal or plasmid-coded alcohol dehydrogenase, and, thus, are capable of hydroxylating ethyl groups from aromatic 5- or 6-member ring heterocycles to the corresponding hydroxyethyl derivative. The heterocycle is used as substrate for the reaction. The hydroxyethyl derivative is not further metabolized.

Suitably, the microorganisms contain the alkBFGH genes of a Pseudomonas OCT plasmid, which code for the alkane hydroxylase complex. In this way, the alkC genes or other genes, which code for active alcohol dehydrogenase, are suitably removed or deactivated.

Source Of The Alkane Monooxygenase Genes

The OCT plasmid of, *Pseudomonas oleovorans* or other microorganisms using alkanes is used as a source of the alkane monooxygenase genes.

Also suitable are structured hybrid plasmids with the alkane monooxygenase genes, which are contained in other microorganisms, such as, in *E. coli* or in *Pseudomonas putida*. As such a hybrid plasmid, for example, plasmid pGEc41, (see FIG. 1), deposited either in *E. coli* DH1 (CBS 102-87) or deposited in *E. coli* DH1

(DSM 6726), can be used. The newly structured hybrid plasmid pGMK921, (see FIG. 3), deposited either in *Pseudomonas putida* PpS81 (DSM 6776) or in *Pseudomonas putida* GPO12 (DSM 6775) can also be used as a source for the alkane monooxygenase genes.

The genetic data, which codes for the alkane monooxygenase, can be obtained by (a) either the OCT plasmid DNA or the hybrid plasmid DNA being isolated from microorganisms, then (b) this DNA being digested for the isolation of the alkane monooxygenase gene and this specific gene sequence then (c) being introduced in an expression vector, and as a result a hybrid plasmid (d) resulting. This hybrid plasmid can then be introduced in a microorganism (e) suitable for the process (host strain) by transformation (f). This transformed host strain (e) then forms production strain (g) for the process according to the invention.

(A) Isolation Of The OCT Plasmid DNA (Hybrid Plasmid DNA)

Both the OCT plasmid DNA and the hybrid plasmid DNA can be obtained according to methods usual to one skilled in the art. In this way, for example, the microorganism is completely lysed, and the desired plasmid DNA can then be obtained by density gradient centrifugation. In this connection, for example, reference can be made to the textbook "Current Protocols In Molecular Biology", Ausubel et al., Eds., J. Wiley, New York, (1989), Section 1.7.

(B) Cleavage Of The Plasmid DNA With Restriction Enzymes

After the isolation of the plasmid DNA, the latter can be cleaved, according to methods usual to one skilled in the art, with restriction enzymes, so that the DNA forms no plasmid-coded alcohol dehydrogenase. The thus-obtained DNA section (alkBFGH), which codes for the active alkane monooxygenase, then can be isolated, for example, by agarose-gel-electrophoresis.

(C) Ligation Of The DNA Section In Expression Vectors

The thus-obtained gene section alkBFGH can be ligated by usual molecular biological techniques with an expression vector DNA previously cut in a like manner, as described, for example, in M. Kok et al., J. Biol. Chem., 264, (1989), pages 5442 to 5451. Expression vectors usually contain a suitable, mostly controllable promoter. One or more singular cutting sites for restriction enzymes lie behind this promoter, advantageously in transcription direction. Then, usually the desired gene section, in whose expression there is interest, is inserted in these cutting sections. The transcription of the alkBFGH genes can be initiated both by the alk promoter under natural regulation (pGEc41) or both by the promoter tacI and the alk promoter under natural regulation (pGMK921). Basically, all expression vectors are suitable which are able to replicate and to express gene section alkBFGH in the selected host.

(D) Hybrid Plasmids

The hybrid plasmids suitably thus resulting comprise in particular a broad host spectrum and can consequently be used in host strains with a high substrate and feedstock tolerance.

In particular, hybrid plasmid pGEc41 is used, which was deposited in *E. coli* DH1 both on Jan. 15, 1987, with the "Centralbureau voor Schimmelcultures at Baarm" in the Netherlands, with deposit number CBS 102-87 and on Sep. 30, 1991, in the Deutschen Sammlung fuer Mikroorganismen und Zellkulturen GmbH [German Collection for Microorganisms and Cell Cultures GmbH] (DSM), Mascheroderweg 1b, D-3300 Brunswick, with deposit number DSM 6726.

Another preferred suitable hybrid plasmid is hybrid plasmid pGMK921, (see FIG. 3), which was deposited both in Pseudomonas putida PpS81 (DSM 6776) and in *Pseudomonas putida* GPO12 (DSM 6775) on Nov. 6, 1991 with the DSM. This hybrid plasmid according to the invention represents a further development of already known hybrid plasmid pGEc285 [*J. Biol. Chem.*, 264, (1989), pages 5442 to 5451]. The structure of hybrid plasmid pGMK921 is diagrammatically represented in FIG. 2.

(E) Host Strains

The thus-obtained hybrid plasmids can be used in many host strains. Suitably host strains with high substrate and feedstock tolerance are used, such as, microorganisms of the genus Pseudomonas, Acinetobacter, Rhizobium, Agrobacterium or Escherichia. Preferably, *E. coli* DH1, *Pseudomonas putida* PpS81 or *Pseudomonas putida* GPO12 is used as the host strain.

F. Transformation

The transformation of host cells with the hybrid plasmids, from which the production strains according to the invention result, is also described in a way known in the art and in detail in the above-identified textbook (i.e., "Current Protocols In Molecular Biology", ibid.).

G. Production Strains

As production strains, all host strains can be used which are transformed with the hybrid plasmids which contain gene section alkBFGH. The natural regulation of the alk-operon can be maintained or decoupled. In particular, *E. coli* DH1, transformed with hybrid plasmid pGEc41 (CBS 102-87 or DSM 6726), *Pseudomonas putida* PpS81 (DSM 6776) or *Pseudomonas putida* GPO12 (DSM 6775), both transformed with hybrid plasmid pGMK921, or active mutants of these strains, are used as production strains. The natural regulation of the alk-operon (alkR=alkST) is maintained in these production strains.

Selection Of The Transformed Microorganisms
(Production Strains)

The isolation (selection) of the transformed host cells takes place advantageously from a selective nutrient medium, to which the biocide is added, against which the labeling-gene contained in the hybrid plasmid provides resistance. If, as preferred, hybrid plasmid pGEc41 contains the tetracycline resistance gene, tetracycline is consequently added to the nutrient medium. In the case of hybrid plasmid pGMK921, which contains the streptomycin-resistance gene, streptomycin is consequently added to the nutrient medium. Cells, which do not contain this hybrid plasmid, are inhibited in growth in such a medium.

Fermentation Process

According to the invention, all strains which are transformed with a hybrid plasmid, which contains gene section alkBFGH, such as, transformed microorganisms of the genus Pseudomonas, Acinetobacter, Rhizobium, Agrobacterium or Escherichia, can be used as production strains. The fermentation process according to the invention is explained below with production strain *E. coli* DH1, transformed with hybrid plasmid pGEc41.

As the substrates, ethylated, aromatic 5- or 6-member ring heterocycles, which contain one or more heteroatoms from the group of oxygen, nitrogen and sulfur, can be used for the reaction. As the aromatic 5-member ring heterocycles, for example, ethylated thiophene derivatives, ethylated furan derivatives, ethylated pyrrole derivatives, ethylated thiazole derivatives, ethylated pyrazole derivatives or ethylated imidazole derivatives can be used. Suitable aromatic 6-member ring heterocycles are, for example, ethylated pyridine derivatives, ethylated pyrimidine derivatives, ethylated pyrazine derivatives or ethylated pyridazine derivatives. In particular, derivatives from the family of compounds of pyrazines or pyridines are used as aromatic, ethylated 6-member ring heterocycles.

With *E. coli* DH1 containing pGEc41 as a production strain, the enzymes of the alk-operon responsible for the hydroxylation can be induced with compounds, which are already described in Grund et al., J. Bacteriol., (1975), 123, pages 546 to 556. They include compounds, which are used, as a carbon and energy source for *Pseudomonas oleovorans*, such as, alkanes, alkanols or alkylated, cyclic compounds. As the alkanes, for example, octane, dodecane or hexane can be used. As the alkanols, for example, octanol, dodecanol or hexanol can be used. As a representative of the alkylated, cyclic compounds, ethylbenzene can be used. Compounds which, for example, do not use *Pseudomonas oleovorans* as a carbon and energy source, but which still induce the genes of the alk-operon, are, for example, dicyclopropylketone, dicyclopropylmethanol or diethoxyethane. Preferably, the enzyme induction with *E. coli* DH1 containing pGEc41 is performed with dicyclopropylketone. The reaction of the substrate can take place both in the presence of the enzyme inductor and in the absence of the enzyme inductor.

For the growth of said production strain, all carbon and energy sources usual to one skilled in the art can be used, such as, sodium succinate. Suitably, tetracycline is added to the cultivation medium to stabilize plasmid pGEc41 before the reaction of the substrate (in the case of the cell cultivation). As a cultivation medium, the media usual among experts, such as, a complex medium ("Nutrient Broth No. 2", Oxoid Ltd., England) or a mineral salt medium, as described in Kulla et al., Arch. Microbiol. (1983), 135, pages 1 to 7, are used.

Before the addition of substrate, the cells are cultivated in the usual way and then the reaction of the substrate suitably is performed at an optical density of 1 to 200 at 650 nm in the culture medium, preferably at an optical density of 5 to 100 at 650 nm.

The reaction can take place either with single or continuous substrate addition, so that the substrate concentration in the culture medium does not exceed 20 percent (w/v). Preferably, the substrate addition takes place so that the substrate concentration in the culture medium does not exceed 5 percent (w/v), in particular 1 percent (w/v). The reaction is performed suitably in a pH range of 4 to 11, preferably 6 to 10. The reaction is usually performed at a temperature of 15° to 50°C., preferably at a temperature of 25° to 40° C. Suitably, the reaction is performed over a period of 1 hour up to several days, preferably continuously over several days. After the reaction, the corresponding 2-hydroxyethyl derivatives can be isolated in a known way, such as, by extraction.

EXAMPLE 1

*E. coli* DH1 (pGEc41), [CBS 102-87], was cultured in a mineral salt medium [Kulla et al., Arch. Microbiol. (1983), 135, pages 1 to 7] with 0.6 percent (w/v) sodium succinate as the sole carbon and energy source. To stabilize the plasmid, 25 mg/l of tetracycline was added to the medium. As the enzyme inductor, dicyclopropylketone was used in a concentration of 1 mmol/l. For cell suspension (100 ml) with an optical density of 10 at 650 nm, 1 mmol of 5-ethyl-2-methylpyridine, which corresponded to a concentration of 0.12 percent (w/v), was added and the cell suspension was incubated for another 16 hours at a temperature of 30° C. and at a pH of 7. Under these conditions, 1 mmol (121 mg/100 ml) of 5-ethyl-2-methylpyrimidine was reacted to 0.8 mmol of 5-(2-hydroxyethyl)-2-methylpyridine, corresponding to a yield of 80 percent, relative to the 5-ethyl-2-methylpyridine used.

Suitably, the reaction was performed with *E. coli* DH1 (pGEc41), [DSM 6726].

EXAMPLES 2 and 3

Examples 2 and 3 were performed according to Example 1 and are summarized in Table 1.

TABLE 1

| Example | Substrate | Concentration of The Substrate per 100 ml | Reaction Time In Hours | End Product | Yield In % |
|---|---|---|---|---|---|
| 2 | 3-ethyl-pyridine | 1 mmol | 16 | 3-(2-hydroxy-ethyl-pyridine | 50 |
| 3 | 2-ethyl-pyrazine | 1 mmol | 16 | 2-(2-hydroxy-ethyl-pyrazine | 80 |

EXAMPLE 4

Figure 2:
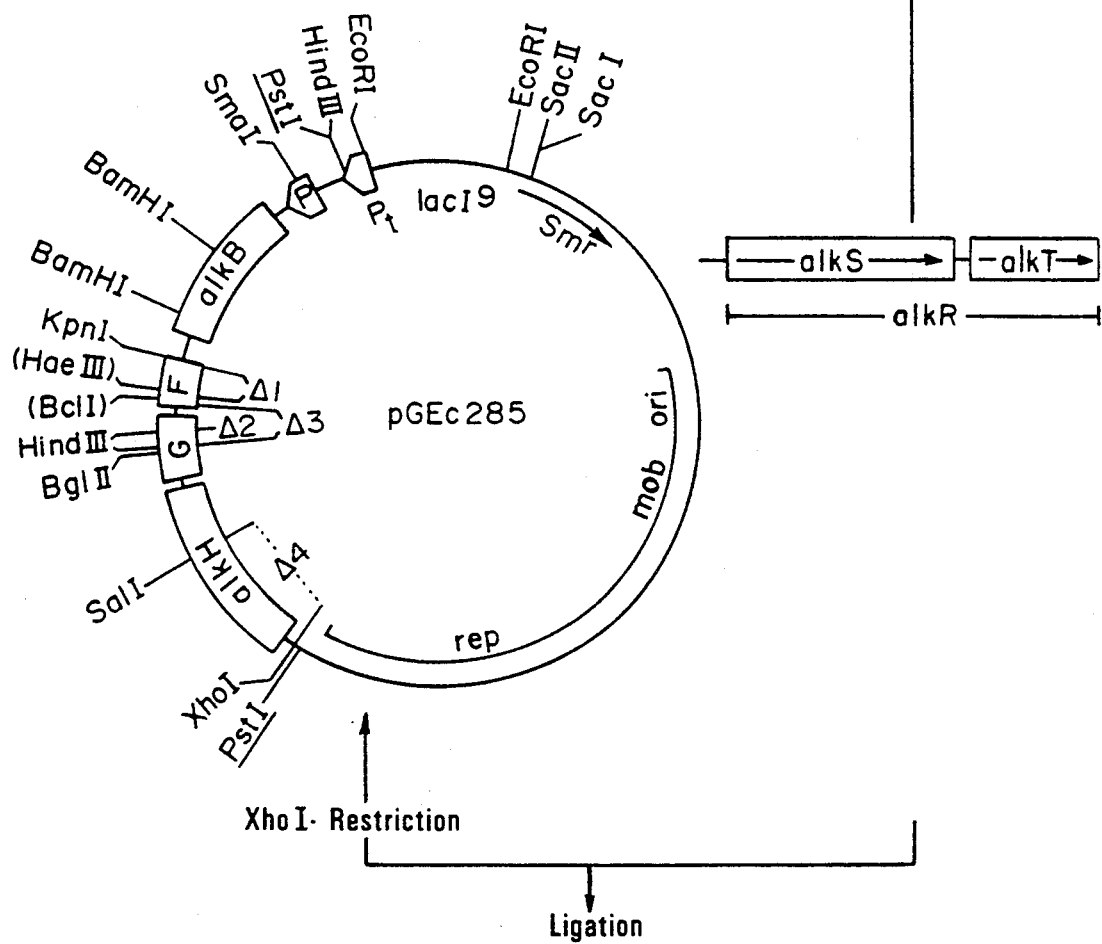
FIG. 2 is a structural diagram of pGMK921.
Figure 2:
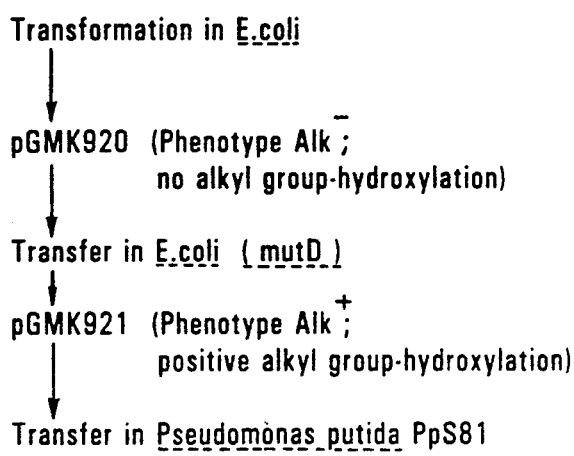

I. Structure of Hybrid Plasmid pGMK921 (FIG. 2)

The structure of pGMK921 is a regulative further development of pGEc285 (see FIG. 2). pGEc285 is described in M. Kok et al., J. Biol. Chem. (1989), 264, pages 5442 to 5451. This plasmid is a derivative of the "multicopy number broad host range" vector pMMB24 [*Gene*, 26 (1983), pages 273 to 282] and contains a PstI-DNA fragment of the OCT plasmid respectively from pGEc41 [*J. Biol. Chem.*, 262, (1987), pages 17712 to 17718], which codes for the cytoplasmatic membrane component of the alkane hydroxylase (AlkB), two rubredoxins (AlkF, AlkG) and for an aldehyde dehydrogenase (AlkH). Transcription of alkBFGH (=alkBA) can be initiated both by the alk-promoter and by the tacI promoter. For the gene expression by the alk-promoter under natural regulation, the alkST-cistrons (=alkR) of the OCT plasmid or of pGEc41 were ligated into pGEc285.

pGEc41 was cut with SalI (4 units per microgram of plasmid DNA) and the DNA fragments were separated by preparative agarose gel electrophoresis [0.6 percent (w/v) agarose in TBE buffer (0.09 M of tris-borate, 2.5 mM of Na$_2$EDTA, pH 8.3, ethidium bromide (100 micrograms/100 ml)]. The 2.5 kb SalI fragment, which codes for alkST, was isolated directly from the agarose gel by a DEAE cellulose membrane The accumulated DNA was washed from the membrane by 0.5 ml of elution buffer (20 mM of tris-HCl, pH 7.5, 1 mM of Na$_2$EDTA, 1.5 M of NaCl) for 1 hour at 65° C. The ethidium bromide was extracted with H$_2$O-saturated n-butanol from the DNA sample and the DNA was then precipitated with isopropanol. The dried precipitate of this fragment preparation designated below as preparation (a) was taken up in 0.01 M tris-HCl buffer, pH 8.0, 0.001 M Na₂EDTA.

pGEc285 was cut with XhoI (4 units per microgram of plasmid DNA) and also precipitated. The dried plasmid preparation, designated below as preparation (b), was taken up in the same buffer.

Both preparations (a) and (b), 0.1-4 microgram of DNA in 20 microliters, were subjected to a Klenow reaction according to instructions (Maniatis et al., Molecular Cloning 1989, Cold Spring Harbor Laboratory Press, Section 5.40 to 5.43). Klenow buffer: 50 mM of tris-HCl, pH 7.5, 10 mM of MgCl₂, 1 mM of dithiothreitol, 50 micrograms/ml of bovine serum albumin.

1 microliter of 0.5 mM of each dNTP (deoxynucleotide triphosphate) was added to the reaction mixture. After adding 1 to 5 units of Klenow polymerase, it was incubated at 30° C. for 15 minutes. Then, the reaction was terminated by heating to 75° C. for 10 minutes.

For ligation, the "blunt ends" (smooth DNA ends without projecting individual strand areas) preparations (a) and (b) were precipitated with isopropanol and taken up in 100 microliters of ligation buffer (20 mM of tris-HCl, pH 7.2, 10 mM of DTT, 10 mM of MgCl₂, 0.6 mM of ATP). The ligation took place after adding T4-DNA ligase (1 unit/microgram of DNA) overnight at 15° C.

It was transformed in E. coli with selection on complex medium with 30 mg of streptomycin per liter of nutrient broth. (Electrotransformation according to Maniatis et al., Molecular Cloning 1989, Cold Spring Harbor Laboratory Press, Section 1.75.) The plasmid received the designation pGMK920 and imparted to the host strain no ability for hydroxylation of alkyl groups. First, the transformation into E. coli [mutD, propagation (exposure of pGMK920) in "mutator background"] and then conjugative transfer (with helper plasmid pRK2013) in Pseudomonas putida, (Ps. putida), PpS81 resulted in an Alk+ phenotype of the plasmid-carrying recipient strain (has the ability to hydroxylate alkyl groups).

For conjugative transfer, E. coli with the alk hybrid plasmid was electrotransformed in addition with helper plasmid pRK2103 (Maniatis et al., ibid.). Selection took place on a complex medium (nutrient broth) with streptomycin 30 mg/l (hybrid plasmid) and kanamycin 25 mg/l (helper plasmid).

1 ml each of this donor culture and the recipient culture (Ps. putida PpS81) were washed several times with nutrient broth, taken up in 50 microliters of nutrient broth each, combined and incubated on dry nutrient broth overnight at 30° C. The cells were suspended in 0.9 percent NaCl solution and suitable dilutions ($10^{-7}$) of $10^9$ cells/ml of suspension were plated out on a selective medium (150 mg of streptomycin per liter). The plasmid now imparting the Alk+phenotype received designation pGMK921.

II. Biotransformation

Production strain Ps. putida PpS81 containing pGMK921 is especially suitable because of the alcA mutation of the host, since the alkane hydroxylase activity is expressed before a completely alcohol dehydrogenase-free background. Ps. putida PpS81 with pGMK921 was cultured on a mineral salt medium [Arch. Microbiol., (1983), 135, pages 1 to 7] with 0.2 percent (w/v) glucose. For plasmid stabilization, streptomycin (150 mg/l ) was added. For induction of the natural promoter for the alkane monooxygenase expression, 1 mM of dicyclopropylketone was added.

At an optical density of $OD_{650nm}=10$ (cultures of lower OD were concentrated to OD=10), 0.1 percent (v/v) of 5-ethyl-2-methylpyrimidine was added to the culture. At a temperature of 30° C. and a neutral pH (7.0), this substrate was reacted after 6 hours completely to 5-(2-hydroxyethyl)-2-methylpyrimidine.

DETAILED DESCRIPTION OF THE DRAWINGS

Regarding FIG. 1:

pGEc41 consists of vector pLAFR1 [Gene, 18, (1982), pages 289 to 296] and a 30 kb EcoRI fragment of OCT plasmid DNA, which codes for a part of the alkBFGHC'-operon (deletion in the alkC gene) and also carries the alkR locus. The fragment reproduced in dots characterizes the deletion downstream in the alkBFGHC'-operon. The boxes convey size and position of the proteins, and the numbers relate to the molecular weight in kilodaltons. In pGEc41, the orientation of the alkR-DNA sequence and the alkBFGHC' sequence is identical [J. Biol. Chem., (1987), 262, pages 17712 to 17718].

Regarding FIG. 2:

It constitutes the structural diagram for the production of pGMK921.

Figure 3:
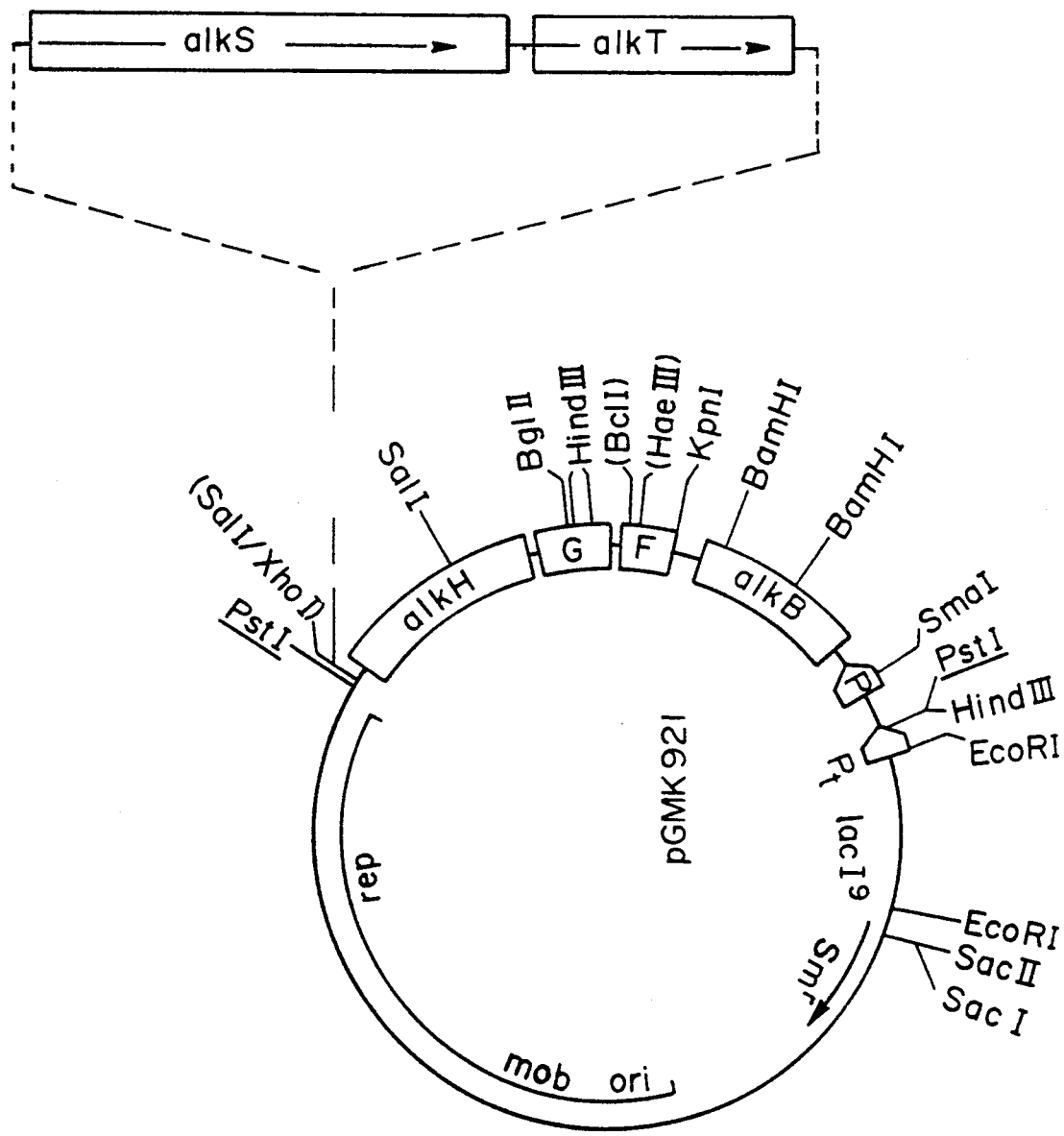
FIG. 3 is a restriction map of pGMK921.

Regarding FIG. 3:

pGMK920 is derived from pGEc285 and pGEc41. The transcription direction of alkBFGH is counterclockwise, and the alkST (alkR) cistrons are transcribed in clockwise direction. The restriction map of pGMK921, which contains an Alk+mutation, is identical with pGMK920. The plasmid codes for:

membrane component of alkane hydroxylase (alkB)
rubredoxin (alkG)
rubredoxin-F (alkF)
aldehyde dehydrogenase (alkH)
rubredoxin reductase (alkS)
positive regulator (alkS)

pGMK921 can be conjugatively transferred from E. coli by helper plasmid (pRK2013) in Pseudomonas. Selection:

streptomycin 35 mg/l (E. coli)
streptomycin 150 mg/l (Pseudomonas putida)

What is claimed is:

1. A microbiological process comprising terminal hydroxylating at least one ethyl group on an aromatic heterocycle, the reaction being performed with a microorganism which:
   (a) contains alkBA genes of Pseudomonas OCT plasmid which forms an active alkane monooxygenase,
   (b) forms no active chromosomal or plasmid-coded alcohol dehydrogenase, and is capable of hydroxylating ethyl groups from an aromatic 5- or 6-member ring heterocycle to the corresponding hydroxyethyl derivative, the heterocycle being used as substrate for the reaction, and the hydroxyethyl derivative not being further metabolixed.

2. The process according to claim 1 wherein the reaction is performed with a microorganism, which belongs to the genus Pseudomonas, Acinetobacter, Rhizobium, Agrobacterium or Escherichia.

3. The process according to claim 2 wherein the reaction is performed either with E. Coli DH1 (CBS 102-87) or with E. coli DH1 (DSM 6726), each transformed with hybrid plasmid pGEc41, or an active mutant of one of these strains.

4. The process according to claim 2 wherein the reaction is performed either with *Pseudomonas Putida* PpS81 (DSM 6776) or with *Pseudomonas Putida* GPO12 (DSM 6775), each transformed with hybrid plasmid pGMK921, or with an active mutant of one of these strains.

5. The process according to claim 4 wherein an ethylated, aromatic 5- or 6-member ring heterocycle, which contains at least one heteroatom from the group consisting of oxygen, nitrogen and sulfur, is used as the substrate.

6. The process according to claim 5 wherein an ethylated pyrazine or an ethylated pyridine is used as the substrate.

7. The process according to claim 6 wherein the reaction takes place with single or continuous substrate addition, so that the substrate addition does not exceed 20 percent (w/v).

8. The process according to claim 7 wherein the reaction is performed at a pH of 4 to 11.

9. The process according to claim 8 wherein the reaction is performed at a temperature of 15° to 50° C.

10. The process according to claim 1 wherein the reaction is performed either with *E. coli* DH1 (CBS 102-87) or with *E. Coli* DH1 (DSM 6726), each transformed with hybrid plasmid pGEc41, or an active mutant of one of these strains.

11. The process according to claim 1 wherein the reaction is performed either with *Pseudomonas putida* PpS81 (DSM 6776) or with *Pseudomonas putida* GPO12 (DSM 6775), each transformed with hybrid plasmid pGMK921, or with an active mutant of one of these strains.

12. The process according to claim 1 wherein an ethylated, aromatic 5- or 6-member ring heterocycle, which contains at least one heteroatom from the group consisting of oxygen, nitrogen and sulfur, is used as the substrate.

13. The process according to claim 1 wherein an ethylated pyrazine or an ethylated pyridine is used as the substrate.

14. The process according to claim 1 wherein the reaction takes place with single or continuous substrate addition, so that the substrate addition does not exceed 20 percent (w/v).

15. The process according to claim 1 wherein the reaction is performed at a pH of 4 to 11.

16. The process according to claim 1 wherein the reaction is performed at a temperature of 15° to 50° C.

17. Hybrid plasmid pGMK921 as deposited in *Pseudomonas putida* PpS81 (DSM 6776).

18. Hybrid plasmid pGMK921 as deposited in *Pseudomonas putida* GPO12 (DSM 6775).

19. Biologically pure culture of *Pseudomonas putida* PpS81 (DSM 6776) transformed with the hybrid plasmid pGMK921.

20. Biologically pure culture of *Pseudomonas putida* GPO12 (DSM 6775) transformed with the hybrid plasmid pGMK921.

21. Hybrid plasmid pGMK921.

* * * * *